(12) United States Patent
Shibata et al.

(10) Patent No.: US 8,958,062 B2
(45) Date of Patent: Feb. 17, 2015

(54) DEFECT INSPECTION METHOD AND DEVICE USING SAME

(75) Inventors: Yukihiro Shibata, Fujisawa (JP); Toshiyuki Nakao, Yokohama (JP); Yuta Urano, Yokohama (JP); Toshifumi Honda, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 185 days.

(21) Appl. No.: 13/701,834

(22) PCT Filed: Jul. 1, 2011

(86) PCT No.: PCT/JP2011/065212
§ 371 (c)(1),
(2), (4) Date: Aug. 26, 2013

(87) PCT Pub. No.: WO2012/017761
PCT Pub. Date: Feb. 9, 2012

(65) Prior Publication Data
US 2014/0009755 A1 Jan. 9, 2014

(30) Foreign Application Priority Data

Aug. 4, 2010 (JP) ................................ 2010-175315

(51) Int. Cl.
*G01N 21/00* (2006.01)
*G01N 21/956* (2006.01)
*G01N 21/88* (2006.01)
*G01N 21/95* (2006.01)

(52) U.S. Cl.
CPC .......... *G01N 21/956* (2013.01); *G01N 21/8806* (2013.01); *G01N 21/9501* (2013.01)

USPC ....................................................... 356/237.5

(58) Field of Classification Search
USPC ....................................................... 356/237.5
See application file for complete search history.

(56) References Cited

U.S. PATENT DOCUMENTS 7,567,343 B2 * 7/2009 Ohshima et al. ........... 356/237.3
(Continued)

FOREIGN PATENT DOCUMENTS

JP 2000-107875 4/2000
(Continued)

*Primary Examiner* — Roy M Punnoose
(74) *Attorney, Agent, or Firm* — Antonelli, Terry, Stout & Kraus, LLP.

(57) ABSTRACT

In order to enable inspections to be conducted at a sampling rate higher than the pulse oscillation frequency of a pulsed laser beam emitted from a laser light source, without damaging samples, a defect inspection method is disclosed, wherein: a single pulse of a pulsed laser beam emitted from the laser light source is split into a plurality of pulses; a sample is irradiated with this pulse-split pulsed laser beam; scattered light produced by the sample due to the irradiation is focused and detected; and defects on the sample are detected by using information obtained by focusing and detecting the scattered light from the sample. Said defect inspection method is configured such that the splitting a single pulse of the pulsed laser beam into a plurality of pulses is controlled in such a manner that the peak values of the split pulses are substantially uniform.

13 Claims, 5 Drawing Sheets

(56) References Cited

U.S. PATENT DOCUMENTS

| | | | |
|---|---|---|---|
| 8,634,069 B2 * | 1/2014 | Nakano et al. | 356/237.1 |
| 8,711,347 B2 * | 4/2014 | Honda et al. | 356/237.2 |
| 2003/0081201 A1 | 5/2003 | Shibata et al. | |
| 2006/0290923 A1 | 12/2006 | Nakano et al. | |
| 2007/0070337 A1 * | 3/2007 | Ohshima et al. | 356/237.3 |
| 2011/0149275 A1 | 6/2011 | Nakano et al. | |
| 2013/0114078 A1 * | 5/2013 | Honda et al. | 356/364 |

FOREIGN PATENT DOCUMENTS

| | | |
|---|---|---|
| JP | 2003-130808 | 5/2003 |
| JP | 2007-33433 | 2/2007 |
| JP | 2007-85958 | 4/2007 |
| JP | 2007-232555 | 9/2007 |
| JP | 2008-20356 | 1/2008 |
| JP | 2009-276273 | 11/2009 |

* cited by examiner

DEFECT INSPECTION METHOD AND DEVICE USING SAME

TECHNICAL FIELD

The present invention relates to a defect inspection method of a defect or an extraneous substance of a micro pattern formed on a sample by a thin film process which is represented by a semiconductor manufacturing process or a manufacturing process of a flat panel display and a device using the same.

BACKGROUND ART

An inspection device of a semiconductor device according to a related art has a configuration as disclosed in Patent Literature 1 (Japanese Patent Application Laid-Open No. 2003-130808) and Patent Literature 2 (Japanese Patent Application Laid-Open No. 2007-85958). The inspection device of the semiconductor device disclosed in Patent Literature 1 uses a VUV (vacuum ultraviolet) pulsed laser as a light source. Since pulsed laser light in this range has a low pulse repetition frequency, if the light is used as it is, an inspection speed is lowered. Therefore, Patent Literature 1 discloses a method that splits pulse light which oscillates a laser light source into a plurality of pulses in a delay optical path.

An inspection device of a semiconductor device disclosed in Patent Literature 2 that uses a UV (ultraviolet) laser for pulse oscillation has a configuration that splits a pulsed laser emitted from a light source so as to be irradiated onto the sample in order to suppress damage to the sample by reducing a peak value of the pulse.

CITATION LIST

Patent Literature

Patent Literature 1: Japanese Patent Application Laid-Open Publication No. 2003-130808
Patent Literature 2: Japanese Patent Application Laid-Open Publication No. 2007-85958

SUMMARY OF INVENTION

Technical Problem

In order to improve a sensitivity of detecting a defect on a semiconductor wafer by a scattered light detecting method, it is useful to detect scattered light component from the defect as many as possible. In a Rayleigh scattering region, generally, the scattered light component is inversely proportional to the fourth power of a wavelength and thus it is possible to raise an intensity of the scattered light component from the defect by shortening the wavelength. As a high power and short wavelength light source which is applicable to the inspection, a 248 nm (KrF) excimer laser or a 193 nm (ArF) excimer laser in the DUV region and a 157 nm (F2) laser may be used. Such gas lasers have an advantage of a high power. However, a pulse oscillating frequency is approximately several kHz and is triple digits or more slower than a sampling frequency (several MHz or higher) of the scattered light component for the inspection. Therefore, if the scattered light component is sampled so as to correspond to an illumination pulse, the inspection time is delayed.

As a method that uses the pulsed laser light source in the inspection device, a method that splits a laser emitted from the pulsed laser light source into a plurality of pulses in the middle of the optical path so as to be irradiated onto the sample is disclosed in Patent Literatures 1 and 2. However, an object of Patent Literature 1 and 2 is to reduce a peak value of the pulse. Therefore, Patent Literatures 1 and 2 do not disclose that the sample is inspected at a higher sampling rate than the pulse oscillation frequency of the pulsed laser emitted from the pulsed laser light source.

Further, in order to make scattered light component from the defect highly sensitive to be proportional to the intensity of the laser light, the intensity of the laser light is increased. However, if a wafer is illuminated by a pulse, damage to the wafer due to instantaneously raised temperature of the wafer caused by the pulse peak value and a wafer damage to the wafer due to an average raised wafer temperature by continuous pulse illumination may occur, which becomes a constraint condition on an increase in the intensity of the laser light. Therefore, it is necessary to perform the inspection while maintaining the illumination intensity so as to be below a critical illumination intensity that accepts the damage caused by the instantaneously raised temperature and the average raised temperature.

In addition, various defects are present on the wafer and the wafer manufacturing process or the semiconductor device manufacturing process have increased needs to stably detect the various defects. Depending on the size or shape of the defects, the scattering distribution of the defects is variedly changed. Therefore, an optical system needs to have a configuration that is capable of detecting the scattered light component even when the defect scattering distribution is varied.

An object of the invention is to address the problems of the above-mentioned related art and provide a defect inspection device and a defect inspection method of a semiconductor device which are capable of inspecting a defect without causing damage on a sample at a sampling rate which is higher than a pulse oscillation frequency of a pulsed laser emitted from a pulsed laser light source.

Solution to Problem

In order to achieve the object, the present invention provides a defect inspection method which includes: splitting a single pulse of a pulsed laser beam emitted from a laser light source into a plurality of pulses to form a pulse-split pulsed laser beam; irradiating the pulse-split pulsed laser beam on a sample; focusing and detecting a scattered light generated from the sample by the irradiating of the pulse-split pulsed laser beam; and detecting a defect on the sample using information obtained by focusing and detecting the scattered light generated from the sample. The splitting of the single pulse of the pulsed laser beam into a plurality of pulsed is controlled so as to maintain a peak value of the pulse-split pulsed laser beam to be substantially constant.

Further, in order to achieve the object, the present invention provides a defect inspection device including: a laser light source that emits a pulsed laser; a pulse splitting unit that splits a single pulse of pulsed laser beam emitted from the laser light source into a plurality of pulses to form a pulse-split pulsed laser beam; an irradiating unit that irradiates the pulsed laser beam which is split by the pulse splitting unit onto a sample; a scattered light detecting unit that focuses a light scattered from the sample onto which the pulse-split pulsed laser beam is irradiated by the irradiating unit to detect the scattered light; and a signal processing unit that detects a defect on the sample using information obtained by focusing and detecting the scattered light from the sample by the scattered light detecting unit. The pulse splitting unit includes a pulse splitting optical path configured to split the single pulse of the pulsed laser beam into a plurality of split pulses and a pulse peak value controller that controls a peak value of the puls-split pulsed laser beam emitted from the pulse splitting optical path so as to be substantially constant.

Advantageous Effect of Invention

According to the present invention, it is possible to inspect a defect at a high speed without substantially lowering a substantial sampling frequency even when a pulse light source having a lower repetition frequency than a sampling frequency of scattered light component is used. Further, by simultaneously illuminating a plurality of viewing fields under the same illumination condition, it is possible to inspect the defect at a high speed. Furthermore, by simultaneously illuminating a plurality of viewing fields under different optical conditions, it is possible to inspect a variety of defects with high sensitivity.

DESCRIPTION OF EMBODIMENTS

First Embodiment

Figure 1:
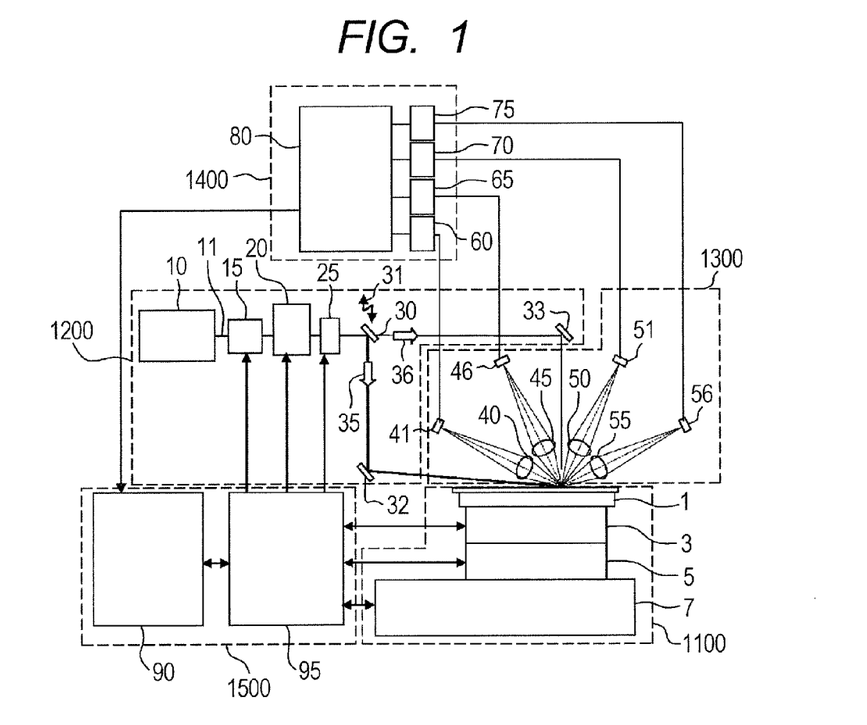
FIG. 1 is a block diagram schematically illustrating an overall configuration of an inspection device.

A configuration of a semiconductor wafer defect inspection device according to an embodiment of the present invention will be illustrated in FIG. 1.

The semiconductor wafer defect inspection device includes a stage unit 1100 on which a semiconductor wafer 1 to be inspected is mounted, an illumination optical system 1200 that irradiates illumination light onto the semiconductor wafer 1 to be inspected, a scattered light detection optical system 1300 that detects the scattered light component from the semiconductor wafer 1 onto which the illumination light is irradiated, a signal processing unit 1400 that processes an output signal from the scattered light detection optical system 1300 that detects the scattered light component, and a controller 1500 that controls entire components.

The stage unit 1100 includes a chuck 2 that supports the semiconductor wafer 1 to be inspected, a rotary stage 3 on which the chuck is mounted, a Z stage 5 which is movable in a height direction, an X stage 6 which is movable in an X-axis direction on a plane, and a Y stage 7 which is movable in a Y-axis direction which is perpendicular to the X-axis direction on the plane.

The illumination optical system 1200 includes a laser light source 10 that oscillates a pulsed laser, an attenuator 15, a pulse splitting optical path 20 that splits a pulse of the pulsed laser, a polarizer 25, and mirrors 30, 32, and 33.

The scattered light detection optical system 1300 includes objective lenses 40, 45, 50, and 55 that are disposed in a plurality of positions at different elevation angles and azimuth angles and sensors 41, 46, 51, and 56 that detect an optical image formed by each of the objective lenses.

The signal processing unit 1400 includes A/D converters 60, 65, 70, and 75 that A/D convert outputs of the sensors 41, 46, 51, and 56 and a signal processor 80 that processes a signal converted by each of the A/D converters.

The controller 1500 includes a mechanical controller 95 that controls a movement of movable mechanisms such as the respective stages of the stage unit 1100 or the attenuator 15, the pulse splitting optical path 20, the polarizer 25, and the mirrors 30 of the illumination optical system 1200 and an operating unit 90.

Hereinafter, operations of the units configured as described above will be described. The semiconductor wafer 1 to be inspected is adsorbed on the chuck 2 and the chuck 2 is mounted on the rotary stage 3, the Z stage 5, and an X stage 7. The rotary stage 3 using a spindle is considered and the highest rotational velocity is approximately 1,000 to 100,000 rpm. The wafer 1 is thoroughly inspected by the rotational movement and a linear movement in a horizontal direction by the X stage 7. Further, it is also possible to thoroughly inspect the wafer by a scanning unit which uses an XYZ orthogonal triaxial stage.

As the illumination light source for inspection, a laser or a lamp have been used. As the laser light source 10, a solid laser having a wavelength of 532 nm, 355 nm, or 266 nm, or a gas laser of 248 nm (KrF), a 193 nm (ArF), or a 157 nm (F2) may be used.

The pulsed laser beam 11 that oscillates the laser 10 transmits the attenuator 15, the pulse splitting optical path 20, and the polarizer 25 to incident in the mirror 30 that switches an oblique illumination and a vertical illumination. The light which is reflected from the mirror 30 is reflected from the mirror 32 to obliquely illuminate the wafer 1. In the meantime, if the mirror 30 is driven by the mechanical controller 95 to be deviated from the optical path, the light is reflected from the mirror 33 to be guided into an optical path that vertically illuminates the wafer 1 and vertically illuminates the wafer 1. Light scattered from the defect on the wafer 1 by the oblique illumination and the vertical illumination is captured by the objective lenses 40, 45, 50, and 55 which are disposed in the plurality of positions at different elevation angles and azimuth angles and detected by the sensors 41, 46, 51, and 56 which are disposed on the image planes thoseof. As the sensor, a multi anode photo multiplier or a backside illuminating image sensor (including a CCD or CMOS sensor) may be used. An analog signal output from the sensors 41, 46, 51, and 56 that detect the scattered light component from the defect on the wafer 1 is converted into a digital signal by the AD converters 60, 65, 70, and 75 and the signal processor 80 determines a defect candidate. A motorized mechanism of the stage or the optical system is controlled by the mechanical controller 95. The operating unit 90 sets the inspection condition or displays the inspection result in accordance with an operational instruction to the controller or by a user.

Figure 2:
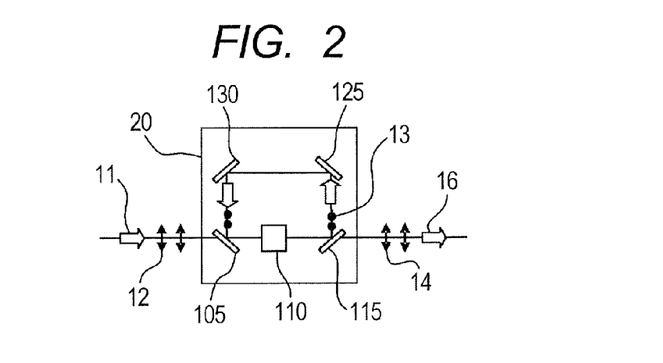
FIG. 2 is a block diagram illustrating a configuration of a pulse splitting optical path.

A configuration of the pulse splitting optical path 20 will be illustrated in FIG. 2. The pulsed laser beam 11 oscillated from the laser light source 10 incidents in a PBS (polarizing beam splitter) 105 of the pulse splitting optical path 20 by P polarization and then incidents in an electro-optical element 110. The electro-optical element 110 is, for example, formed of lithium niobate (LiNbO3) and has a characteristic that causes the light that transmits a lithium niobate element in accordance with a voltage which is applied on both sides of the lithium niobate element to be birefringent so that a polarized face 90 of the pulse light which incidents in the electro-optical element 110 is rotated at approximately 90 degrees to be substantially S polarized on the PBS 115, and some light components are transmitted but most light components are reflected from the PBS 115. The reflected light is reflected from total reflection mirrors 125 and 130, incidents in the PBS 105 as S polarization, and is reflected from the PBS 105. The light which incidents in the electro-optical element 110 at a second cycle has a birefringence which is different from a birefringence of light at a first cycle to rotate the polarized face. In this case, the voltage which is applied to the electro-optical element 110 is controlled so that some light components are transmitted by the PBS 115 and most light is reflected from the PBS 115. The control of the electro-optical element 110 will be described with reference to FIGS. 3, 4, and 5.

Figure 3:
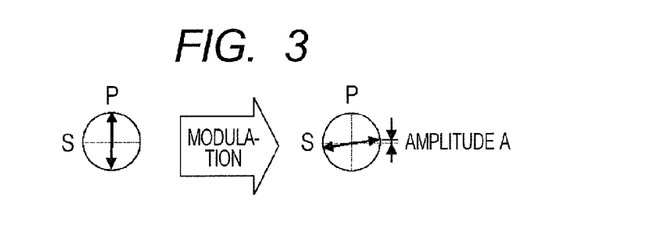
FIG. 3 is a view illustrating a polarization state (left side) of pulse light which incidents in the pulse splitting optical path before arriving on an electro-optical element and a polarization state (right side) of pulse light immediately after being emitted from the electro-optical element.
Figure 4:
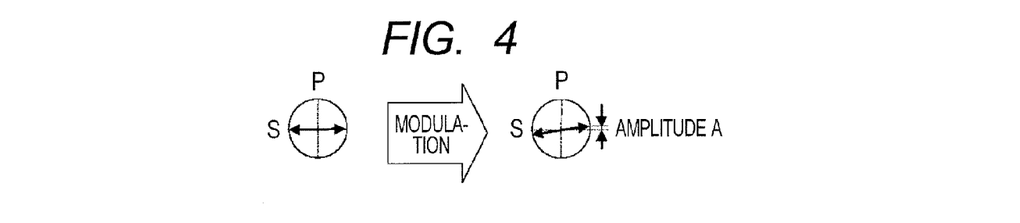
FIG. 4 is a view illustrating a polarization state (left side) of pulse light which travels around the pulse splitting optical path before arriving again on an electro-optical element and a polarization state (right side) of pulse light immediately after being emitted from the electro-optical element.
Figure 5:
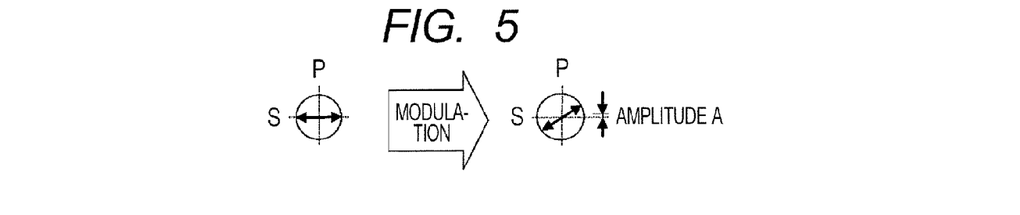
FIG. 5 is a view illustrating a polarization state (left side) of pulse light which travels around the pulse splitting optical path n times before arriving again on an electro-optical element and a polarization state (right side) of pulse light immediately after being emitted from the electro-optical element.

FIG. 3 illustrates a state at the first cycle of the pulse splitting optical path 20 where the pulsed laser beam 11 from the laser light source 10 initially incidents in the electro-optical element 110. The left side of the arrow illustrates a state of the polarization of the laser beam which incidents in the electro-optical element 110 and the right side of the arrow illustrates a state of the polarization of the laser beam which is emitted from the electro-optical element 110 to incident in the PBS 115. The laser beam which incidents in the electro-optical element 110 in a state of P polarization is the light controlled by the voltage which is applied to the electro-optical element 110 so as to rotate the polarization plane at approximately 90 degrees. By doing this, an amplitude of the laser beam that transmits the PBS 115 is referred to as A. FIG. 4 illustrates a state at the second cycle. The laser beam which incidents in the electro-optical element 110 in a state of S polarization is the light controlled by the voltage which is applied to the electro-optical element 110 so that the amplitude of the P polarization laser beam is equal to the transmittance amplitude A at the first cycle. Further, FIG. 5 illustrates a state at an n-th cycle. As the rotation is repeated, an amplitude of laser beam arriving on the electro-optical element 110 becomes smaller as much as the light is deviated from the PBS 115. Therefore, in order to maintain the amplitude A of the light that transmits the PBS 115 to be constant, it is required to control the modulation amount of the electro-optical element 110 whenever the rotation is repeated. The modulation amount of the electro-optical element 110 is controlled by the mechanical controller 95.

Figure 6:
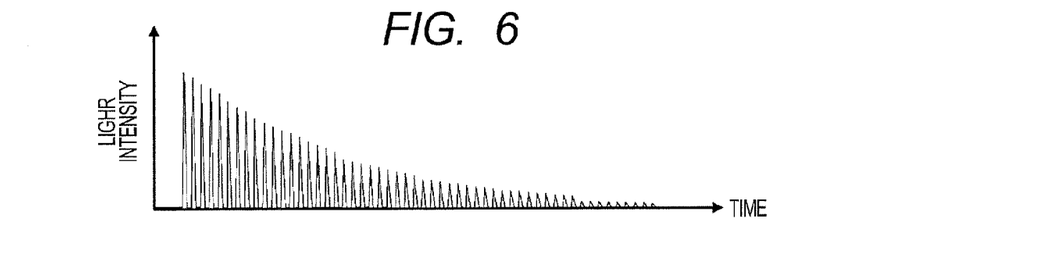
FIG. 6 is a graph illustrating a concept of change of light intensity when light from a single pulse is split by a pulse splitting method according to the related art.
Figure 7:
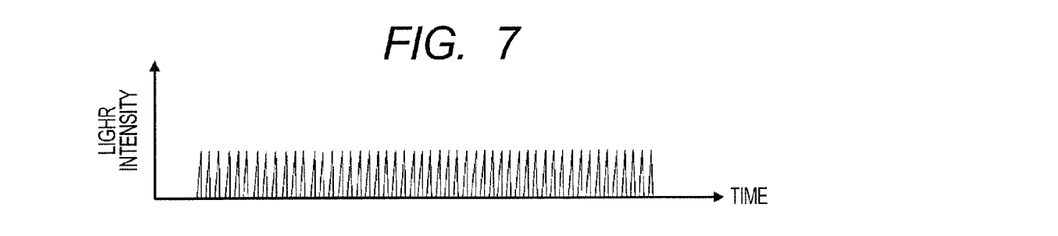
FIG. 7 is a graph illustrating a concept of change of light intensity when light from a single pulse is split by a uniform intensity pulse splitting method according to an embodiment of the present invention.

FIG. 6 illustrates a state of a light intensity when the modulation amount of the electro-optical element 110 is fixed. In this case, light intensity is lowered with time. In contrast, by controlling the modulation for every pulse by the electro-optical element 110, as illustrated in FIG. 7, it is possible to split the pulse to have a uniform intensity. If a length of the pulse splitting optical path 20 (for example, a length where light travels around the pulse splitting optical path 20 from an incident surface of the electro-optical element 110 to reach the incident surface of the electro-optical element 110 again) is 60 cm, the modulation for every pulse may be controlled by the electro-optical element 110 at a driving frequency of 500 MHz.

By increasing the intensity of the illumination light, the scattered light component from the defect is increased in proportion to the intensity. If a noise component for detecting the defect is a roughness of a surface of the wafer, an S/N of defect detection is propositional to 0.5 power of the intensity. The high intensity of the illumination has a trade-off relationship with damage of the wafer or the optical system. Therefore, it is required to increase the intensity while avoiding the damage.

Figure 13:
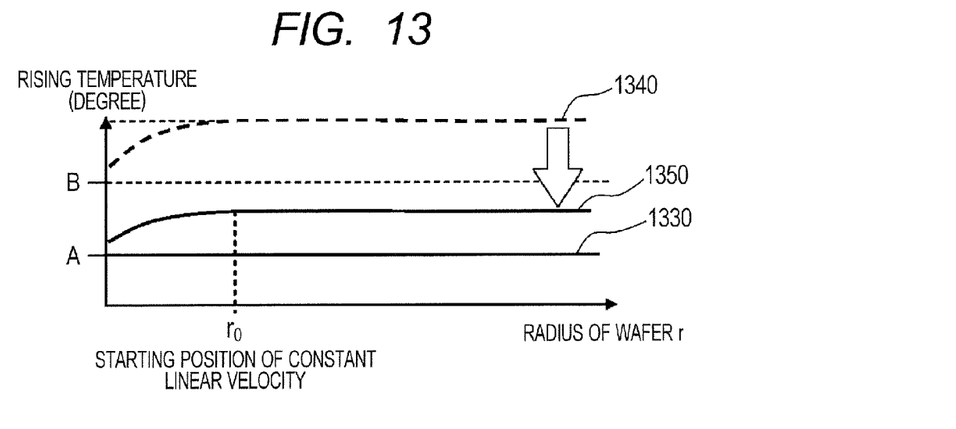
FIG. 13 is a graph illustrating a relationship between an irradiating position of illumination light in a radial direction of a wafer and a temperature of the wafer when the illumination intensity of the illumination light is controlled.

A method that controls the intensity of illumination in accordance with the scanning speed of wafer 1 is illustrated in FIG. 13. The damage of the wafer 1 is an average temperature rising limit A by the laser beam and an instantaneous temperature rising limit B by the peak value of the pulse illumination. The instantaneous temperature rising limit B is higher than the average temperature rising limit A. If the viewing field of the optical system is in an inner circumference of the wafer (a portion close to the center of the wafer), the scanning of the wafer 1 in the viewing field position (laser irradiating location) is slow and thus the temperature of the wafer 1 is easily increased. Therefore, in a position where a linear speed is slow, the illumination intensity is lowered by the attenuator 15 to avoid the damage. As the linear speed is increased, the illumination intensity is correspondingly increased and thus the illumination intensity is constant when the radius is above a radius where the linear speed is constantly controlled.

Figure 14A:
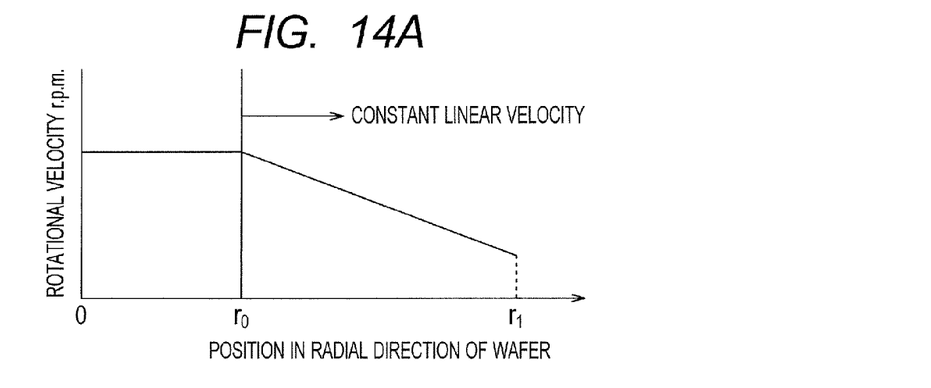
FIG. 14A is a graph illustrating a relationship between an illuminating position in a radial direction of a wafer and a rotational velocity of the wafer.
Figure 14B:
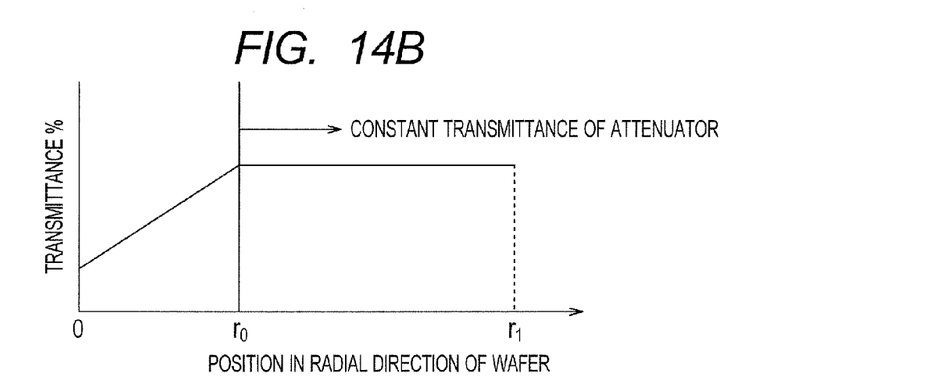
FIG. 14B is a graph illustrating a relationship between an illuminating position in a radial direction of a wafer and a transmittance of an attenuator.

In other words, as illustrated in FIG. 14A, the rotary stage 3 is controlled by the mechanical controller 95 to maximize the rotating speed of the wafer 1 when the inspection is performed from the center of the wafer 1 to the position of a radial direction r0 and to lower the rotating speed of the wafer 1 in accordance with the position of the wafer 1 in the radial direction when the position outside the radial direction r0 is inspected. On the other side, in this case, as illustrated in FIG. 14B, the attenuator 15 is controlled by the mechanical controller 95 to change a light transmittance of the attenuator 15 so as to become smaller as the position approaches the center of the wafer 1 in accordance with the position of the wafer 1 in the radial direction when the inspection is performed from the center of the wafer 1 to the position of a radial direction r0 and to constantly maintain the light transmittance regardless of the position of the wafer 1 in the radial direction when the position outside the radial direction r0 is inspected.

As described above, regardless of the radial position of the wafer, the illumination intensity is controlled to be increased to the limit A of the average temperature rise 1330. In a case that the pulse splitting is not performed, or in a case that the peak value of the split pulse is changed depending on the time similarly to the related art even though the pulse splitting is performed, even if increasing the illumination intensity so that the average temperature rise 1330 is the limit A, the instantaneous temperature rise 1340 may exceed the limit B. In contrast, according to this embodiment, the pulse splitting is performed so that the peak values of the split pulses are substantially constant as illustrated in FIG. 2 to lower the pulse peak value. Therefore, the pulse peak value may be reduced, and thus the instantaneous temperature rise may be reduced to 1350.

Second Embodiment

In the first embodiment, a configuration where a pulse of the pulsed laser beam 11 is split to illuminate the wafer 1 has been described. In a second embodiment, a method that splits a laser beam of which a pulse is split into a plurality of optical paths to illuminate the wafer 1 will be described.

Figure 8:
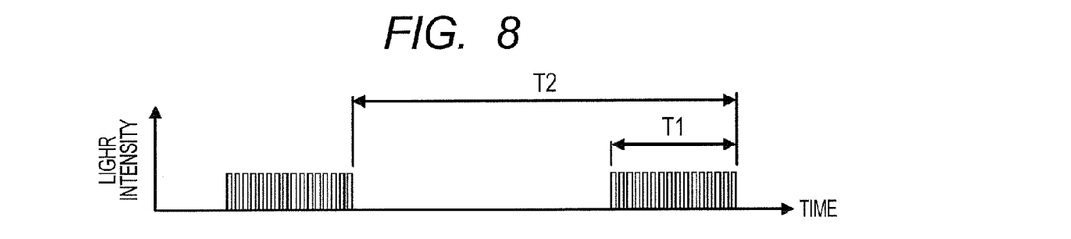
FIG. 8 is a graph illustrating an output state from a pulse splitting optical path when light from a single pulse is split by a uniform intensity pulse splitting method according to an embodiment of the present invention.
Figure 9:
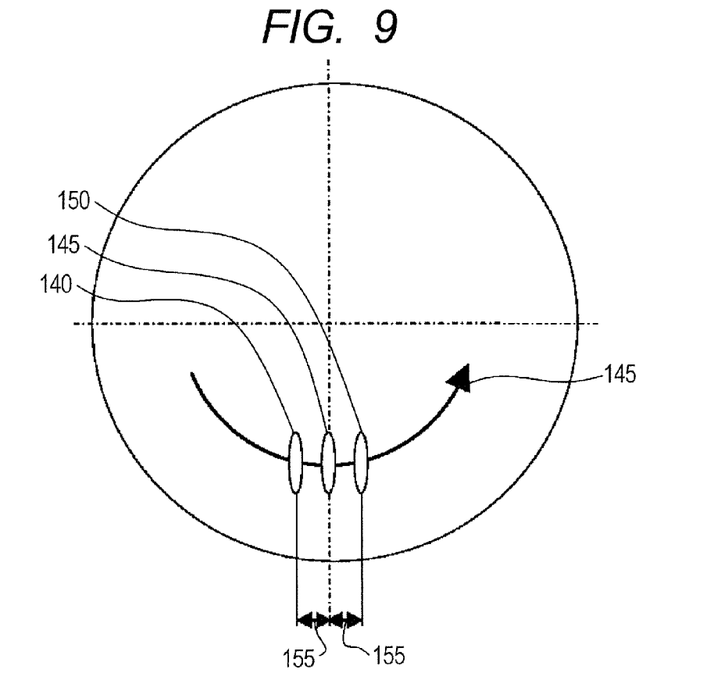
FIG. 9 is a plan view of a wafer illustrating a state where an optical path of illumination light is bifurcated into three to simultaneously illuminate three locations on the wafer.

In FIG. 8, a state of split pulses is illustrated. It is assumed that a period T2 of the pulse that oscillates the pulsed laser beam is three times of T1 which is a split pulse generation time. Also in this case, an example in which the inspection is performed by a uniform motion is illustrated in FIG. 9. The illumination light illuminates three areas 140, 145, and 150 on the wafer 1. The intervals 155 of the three areas correspond to the split pulse generation time T1. Therefore, three viewing fields are simultaneously illuminated for T1 to detect the scattered light component. When a next pulse is irradiated, scattered light component in an area where the scattered light component has not been detected is detected.

Figure 10:
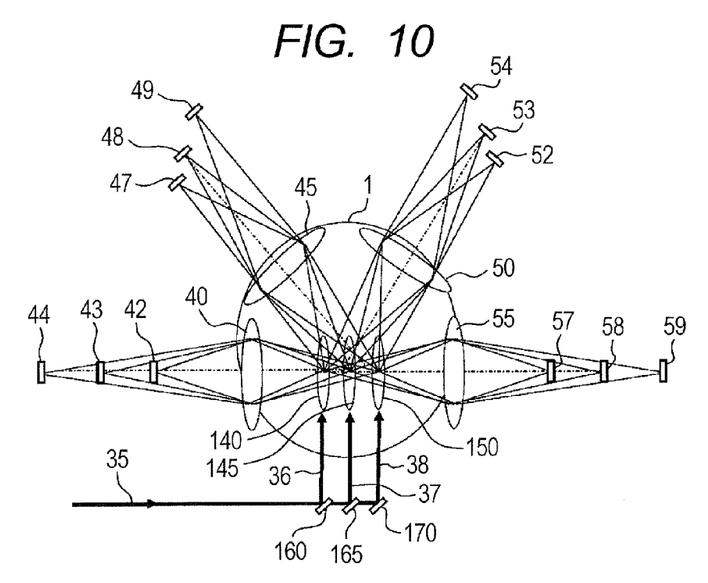
FIG. 10 is a plan view of a wafer and a detection optical system illustrating a schematic configuration in which an optical path of illumination light is bifurcated into three using a mirror to simultaneously illuminate three locations on the wafer and front scattered light component and side scattered light component from the illumination locations are detected by the detection optical systems disposed at four directions.

A configuration of an optical system that simultaneously detects a plurality of viewing fields is illustrated in FIG. 10. The illumination light 35 which is reflected from the mirror 32 with the configuration illustrated in FIG. 1 incidents in the mirror 160. Here, the mirror 160 has a characteristic that transmits two third of the incident light and reflects one third thereof. The illumination light which is reflected from the mirror 160 goes toward the semiconductor wafer 1. The light that transmits the mirror 160 having the above-mentioned characteristic incidents in a half mirror 165 that transmits half of the incident light and reflects the remaining light. The illumination light reflected from the half mirror 165 goes toward the semiconductor wafer 1. The light which transmits the half mirror 165 is reflected by a total reflection mirror 170 to go toward the semiconductor wafer 1. The illumination light which is reflected (split) by the mirror group 160, 165, and 170 having the above-mentioned characteristic illuminates areas 140, 145, and 150 on the semiconductor wafer 1 with the same illumination intensity.

Among light scattered from the area 140 which is illuminated by the illumination light 36 reflected from the mirror 160, light which incidents in the lenses 40, 45, 50, and 55 is focused to be detected by the sensors 44, 49, 52, and 57. Among light scattered from the area 145 which is illuminated by the illumination light 37 reflected from the mirror 165, light which incidents in the lenses 40, 45, 50, and 55 is focused to be detected by the sensors 43, 48, 53, and 58. Further, among light scattered from the area 150 which is illuminated by the illumination light 38 reflected from the mirror 170, light which incidents in the lenses 40, 45, 50, and 55 is focused to be detected by the sensors 42, 47, 54, and 50. For example, from the viewpoint of the lens 40, since the detection viewing fields 140, 145, and 150 are different spaces, images formed by using the lens 40 are also formed in the different positions. Therefore, the sensors 42, 43, and 44 may be disposed in an image plane of each of the viewing fields. Further, the sensors 47, 48, 49, 52, 53, 54, 57, 58, and 59 that individually detect the scattered light component of the viewing field are disposed on the image planes by the lenses 45, 50, and 55. Therefore, also in the image plane by the lenses 45, 50, and 55 where the sensors 42, 43, and 44 may be disposed on the image plane of each viewing field, sensors 47, 48, 49, 52, 53, 54, 57, 58, and 59 that individually detect the scattered light component of the viewing fields are disposed.

Modified Embodiment of Second Embodiment

In the configuration illustrated in FIG. 10, a configuration in which the optical path of the illumination light is split into three using three mirrors 160, 165, and 170 has been described. However, this configuration has a limitation in narrowing the interval of the mirrors. Therefore, the illumination areas 140, 145, and 150 on the wafer 1 may not be closer to each other than the limitation that allows the three mirrors 160, 165, and 170 to be closer.

Figure 11:
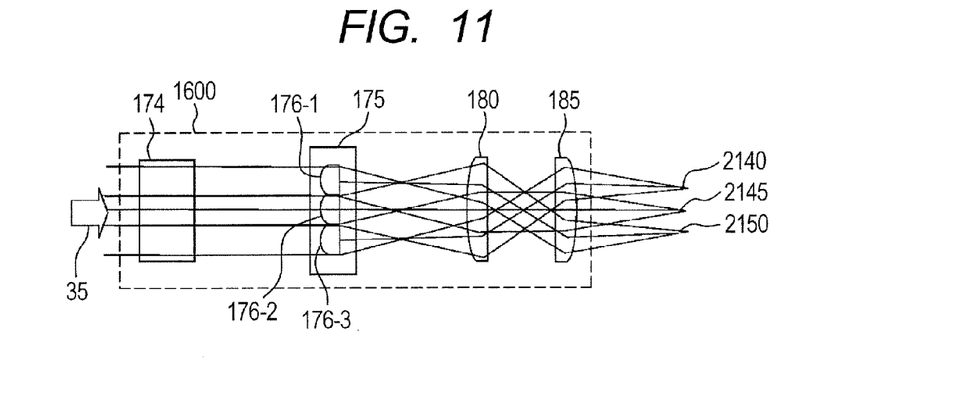
FIG. 11 is a plan view schematically illustrating an optical system that bifurcates the optical path of the illumination light into three by a combination of lenses.

In order to address the problems, using a split illumination optical system 1700 which is provided in the light path of the illumination light 35 reflected from the mirror 32, a configuration of a split illumination optical system 1600 that allows three illumination areas 2140, 2145, and 2150 on the wafer 1 to be closer to each other without broadening a width of light beam is illustrated in FIG. 11. The pulsed laser beam 35 which is reflected from the mirror 32 incidents in an intensity uniformizing element 174 that uniformly distributes the intensity in the cross section of the pulsed laser beam. As an example of the uniformizing element 174, an aspheric lens element or a diffractive optical element may be used. The pulsed laser beam whose intensity distribution in the cross section of the beam is uniformized by the uniformizing element 174 incidents in the lens array 175. The lens array 175 has a plurality of comparatively small-sized lenses 176 to focus plural lights in each of the focal position of the plurality of comparatively small-sized lenses 176 from one incident beam 35. The lights focused by the lenses 176-1 to 176-3 of the lens array 175 are collimated by the lens 180 and focused by the lens 185 in spatially different positions 2140, 2145, and 2150 on the wafer 1. Therefore, it is possible to focus and illuminate the beams in three viewing fields close to each other.

Third Embodiment

Figure 12:
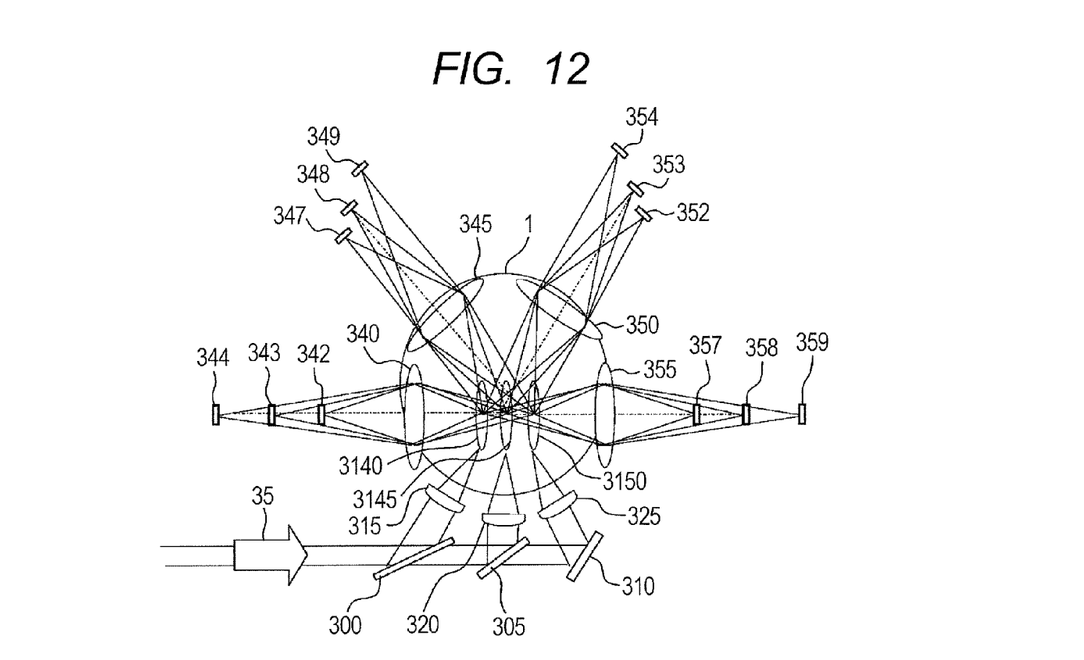
FIG. 12 is a plan view of a wafer and a detection optical system illustrating a schematic configuration in which an optical path of illumination light is bifurcated into three using a mirror and a combination of lenses to simultaneously illuminate three locations on the wafer and a front scattered light component, a side scattered light component, and a back scattered light component from the illumination locations are detected by the detection optical systems disposed at four directions.

In the configuration of FIG. 10 which has been described in the second embodiment, only front and side scattered light component is detected. However, depending on the type of the defect, some defects are strongly backwardly scattering the illuminated light. Therefore, in order to broadly detect the defect, a configuration that separately detects the scattered light component in the front, side, and backside is desirable. As compared with the configuration illustrated in FIG. 10, as a configuration that detects light which is scattered in the front, side, and backside by switching the direction of the illumination light, a configuration having a plurality of illuminations and detecting a plurality of viewing fields is illustrated in FIG. 12.

With the configuration illustrated in FIG. 1, the illumination light (pulsed laser beam) 35 reflected from the mirror 32 incidents in the mirror 300. Here, the mirror 300 has a characteristic that transmits two third of the incident light and reflects one third thereof. The illumination light reflected from the mirror 300 is focused by the lens 315 to illuminate an area 3140 on the wafer 1. Among the illumination light that transmits the mirror 300, half of an amount of the light which incidents in the half mirror 305 is transmitted and the remaining is reflected. The light reflected from the half mirror 305 is focused by the lens 320 to illuminate the area 3145 on the wafer 1. The light that transmits the half mirror 305 is reflected by the total reflection mirror 310 and focused by the lens 325 to illuminate the area 3150 on the wafer 1.

As described above, the directions of the light which illuminates the areas 3140, 3145, and 3150 on the wafer 1 are different from each other. From the viewpoint of the area 3140, the lens 340 focuses the back scattered light component, the lens 345 focuses the side scattered light component, and the lenses 350 and 355 focus the front scattered light component to be detected by the detectors 342 to 344, 347 to 349, 352 to 354, and 357 to 359. Further, from the viewpoint of the area 3145, the lenses 340 and 355 detect the side scattered light component and the lenses 345 and 350 detect the front scattered light component. Furthermore, from the viewpoint of the area 3150, the lenses 340 and 345 detect the front scattered light component, the lens 350 detects the side scattered light component, and the lens 355 detects the back scattered light component. With this configuration, the scattered light component in all directions may be detected, which may efficiently improve a defect capturing rate.

The configuration, the function, and the image processing contents described in the embodiments may be considered to be combined in various ways. However, it is obvious that the combination thereof falls into the scope of the present invention.

INDUSTRIAL APPLICABILITY

The present invention may be applied to a device that inspects a defect such as a defect or an extraneous substance of a micro pattern formed on a sample by a thin film process which is represented by a semiconductor manufacturing process or a manufacturing process of a flat panel display.

REFERENCE SIGNS LIST

1 Wafer
3 θ stage
5 Z stage
7 X stage
10 Laser light source
15 Attenuator
20 Pulse splitting optical path
25 Polarizer
40, 45, 50, 55 Objective lens
41, 46, 51, 56 Sensor
80 Signal processor
90 Operation unit
95 Mechanical controller
105, 115 PBS
110 Electro-optical element
1125, 130 Mirror
174 Intensity uniformizing element in the beam
175 Lens array

The invention claimed is:

1. A defect inspection method, comprising:
splitting a single pulse of a pulsed laser beam emitted from a laser light source into a plurality of pulses to form a pulse-split pulsed laser beam;
irradiating the pulse-split pulsed laser beam on a sample;
focusing and detecting a scattered light generated from the sample by the irradiating of the pulse-split pulsed laser beam; and
detecting a defect on the sample using information obtained by focusing and detecting the scattered light generated from the sample,
wherein in the step of splitting, the splitting of the single pulse of the pulsed laser beam into a plurality of pulses is controlled so as to maintain a peak value of the pulse-split pulsed laser beam to be substantially constant.

2. The defect inspection method according to claim 1, wherein the pulse-split pulsed laser beam is irradiated on the sample by switching an optical path between a high elevation angle direction and a low elevation angle direction with respect to the sample.

3. The defect inspection method according to claim 1, wherein the pulse-split pulsed laser beam is branched into a plurality of optical paths and the pulse-split pulsed laser beam which is branched into the plurality of optical paths is simultaneously irradiated onto the sample from a plurality of directions.

4. The defect inspection method according to claim 1, wherein among the scattered light generated from the sample onto which the pulse-split pulsed laser beam is irradiated, a light component which is scattered to a front of an incident direction of the pulse-split pulsed laser beam onto the sample and a light component which is scattered to a side thereof are separately detected.

5. The defect inspection method according to claim 4, wherein among the scattered light generated from the sample onto which the pulse-split pulsed laser beam is irradiated, a light which is scattered to a back side thereof is also detected.

6. The defect inspection method according to claim 1, wherein while moving an irradiation area of the pulse-split pulsed laser beam on the sample in a radial direction of the rotation in a state where the sample is rotated, detecting the light scattered from the sample includes controlling an intensity of the pulse-split pulsed laser beam in accordance with the radial direction of the rotation of the irradiation area to irradiate the pulse-split pulsed laser beam onto the sample.

7. A defect inspection device, comprising:
a laser light source that emits a pulsed laser beam;
a pulse splitting unit that splits a single pulse of the pulsed laser beam emitted from the laser light source into a plurality of pulses;
an irradiating unit that irradiates the pulsed laser beam which is split by the pulse splitting unit onto a sample;
a scattered light detecting unit that focuses a light scattered from the sample onto which the pulse-split pulsed laser beam is irradiated by the irradiating unit to detect the scattered light; and a signal processing unit that detects a defect on the sample using information obtained by focusing and detecting the scattered light from the sample by the scattered light detecting unit, wherein the pulse splitting unit includes a pulse splitting optical path configured to split the single pulse of the pulsed laser beam into a plurality of split pulses and a pulse peak value controller that controls a peak value of the pulse-split pulsed laser beam emitted from the pulse splitting optical path so as to be substantially constant.

8. The defect inspection device according to claim 7, wherein the pulse peak value controller includes an electro-optical element and a voltage which is applied to the electro-optical element is varied for each of the split pulse of the pulse-split pulsed laser beam which passes through the electro-optical element so that a peak value of the split pulse of the pulse-split pulsed laser beam emitted from the pulse splitting optical path is controlled to be substantially constant.

9. The defect inspection device according to claim 7, further comprising:
    a high elevation angle irradiating unit that irradiates the pulse-split pulsed laser beam emitted from the pulse splitting optical path onto the sample at a high elevation angle;
    a low elevation angle irradiating unit that irradiates the pulse-split pulsed laser beam onto the sample at a low elevation angle; and
    an optical path switching unit that switches an optical path of the pulse-split pulsed laser beam emitted from the pulse splitting optical path between the high elevation angle irradiating unit and the low elevation angle irradiating unit.

10. The defect inspection device according to claim 7, further comprising:
    an optical path branching unit that branches the pulsed laser beam split by the pulse splitting optical path into a plurality of optical paths,
    wherein the irradiating unit includes a plurality of irradiating portions that irradiate the pulse-split pulsed laser beam which is branched into the plurality of optical paths by the optical path branching unit onto the sample to simultaneously irradiate the pulse-split pulsed laser beam from the plurality of directions using the plurality of irradiating portions.

11. The defect inspection device according to claim 7, wherein the scattered light detecting unit includes a front scattered light detecting unit that detects a light which is scattered to a front of an incident direction of the pulse-split pulsed laser beam onto the sample, among the scattered light components generated from the sample onto which the pulse-split pulsed laser beam is irradiated by the irradiating unit; and
    a side scattered light detecting unit that detects a light which is scattered to a side of the incident direction of the pulse-split pulsed laser beam onto the sample.

12. The defect inspection device according to claim 11, wherein the scattered light detecting unit further includes a back scattered light detecting unit that detects a back scattered light which is scattered to a back side of the incident direction of the pulse-split pulsed laser beam onto the sample, among the scattered light generated from the sample onto which the pulse-split pulsed laser beam is irradiated by the irradiating unit.

13. The defect inspection device according to claim 7, further comprising:
    a rotary table unit that mounts and rotates the sample;
    a moving unit that moves the irradiation area on the sample of the pulse-split pulsed laser beam by the irradiating unit in a radial direction of the rotation by the rotary table unit; and
    a pulsed laser beam intensity controller that controls an intensity of the pulse-split pulsed laser beam in accordance with the position in the radial direction of the rotation of the irradiation area of the pulse-split pulsed laser beam when in a state where the sample is rotated by the rotary table, the irradiation area of the pulse-split pulsed lease beam on the sample is moved in the radial direction of the rotation by the moving unit.

\* \* \* \* \*